(12) United States Patent
Manne

(10) Patent No.: US 11,478,602 B2
(45) Date of Patent: *Oct. 25, 2022

(54) TASTE INHIBITION THROUGH THE USE OF AN AIR FLOW

(71) Applicant: JB Scientific, LLC, New York, NY (US)

(72) Inventor: Joseph Manne, New York, NY (US)

(73) Assignee: JB SCIENTIFIC, LLC, New York, NY (US)

( * ) Notice: Subject to any disclaimer, the term of this patent is extended or adjusted under 35 U.S.C. 154(b) by 678 days.

This patent is subject to a terminal disclaimer.

(21) Appl. No.: 16/459,250

(22) Filed: Jul. 1, 2019

(65) Prior Publication Data

US 2019/0321577 A1    Oct. 24, 2019

Related U.S. Application Data

(63) Continuation of application No. 14/777,192, filed as application No. PCT/US2014/027510 on Mar. 14, 2014.

(60) Provisional application No. 61/789,310, filed on Mar. 15, 2013, provisional application No. 61/789,041, filed on Mar. 15, 2013.

(51) Int. Cl.
*A61M 16/12* (2006.01)
*A61K 33/00* (2006.01)
*A61M 16/06* (2006.01)
*A62B 18/00* (2006.01)

(52) U.S. Cl.
CPC ........... *A61M 16/122* (2014.02); *A61K 33/00* (2013.01); *A61M 16/0666* (2013.01); *A62B 18/003* (2013.01)

(58) Field of Classification Search
CPC ...... A61M 16/00; A61M 16/10; A61M 15/00; A61M 15/002; A62B 18/003
See application file for complete search history.

(56) References Cited

U.S. PATENT DOCUMENTS

| | | | |
|---|---|---|---|
| 2,032,101 A | 2/1936 | Sullivan | |
| 2,332,662 A | 9/1942 | Nathanson | |
| 2,560,215 A | 7/1951 | Christensen | |
| 3,683,907 A | 8/1972 | Cotabish | |
| 4,216,769 A * | 8/1980 | Grimes | A61M 16/0666 128/205.25 |
| 4,282,869 A | 8/1981 | Zidulka | |
| 4,406,283 A * | 9/1983 | Bir | A61M 16/0672 128/207.18 |
| 4,521,427 A | 6/1985 | Nietupski | |
| 4,593,688 A * | 6/1986 | Payton | A61M 16/06 128/205.24 |

(Continued)

FOREIGN PATENT DOCUMENTS

WO    89/00874 A1    2/1989
WO    2012123819 A1    9/2012

OTHER PUBLICATIONS

Office Action dated Jul. 20, 2017 from related European Patent Application No. 14768448.4.

(Continued)

*Primary Examiner* — Michael J Tsai
(74) *Attorney, Agent, or Firm* — Lucas & Mercanti, LLP

(57) ABSTRACT

A flow of air is directed at the face and into the nose and mouth so as to decrease taste and inhibit appetite.

17 Claims, 2 Drawing Sheets

(56) References Cited

U.S. PATENT DOCUMENTS

| | | |
|---|---|---|
| 5,048,516 A | 9/1991 | Soderberg |
| 5,353,605 A | 10/1994 | Naaman |
| 5,561,862 A | 10/1996 | Flores, Sr. |
| 6,065,473 A | 5/2000 | Mccombs et al. |
| 6,247,470 B1 * | 6/2001 | Ketchedjian ...... A61M 16/0666 128/207.18 |
| 6,675,796 B2 | 1/2004 | McDonald |
| 7,036,502 B2 | 5/2006 | Manne |
| 7,694,680 B2 | 4/2010 | Brichetto |
| 7,879,584 B2 | 2/2011 | Krishna et al. |
| 2003/0012811 A1 | 1/2003 | Paul |
| 2003/0188743 A1 | 10/2003 | Manne |
| 2004/0055601 A1 | 3/2004 | De Luca et al. |
| 2006/0222720 A1 | 10/2006 | Yamashita |
| 2008/0190436 A1 | 8/2008 | Jaffe et al. |
| 2009/0197963 A1 | 8/2009 | Llewellyn |
| 2010/0239687 A1 | 9/2010 | Kim et al. |

OTHER PUBLICATIONS

Office Action dated Feb. 8, 2017 from related European Patent Application No. 17768448.4.
International Search Report dated Jul. 25, 2014 from related PCT Application No. PCT/US2014/027510.
E.T. Rolls; Taste, olfactory and food texture reward processing in the brain and obesity; Int. Journal of Obesity; vol. 35; No. 4; 201 O; pp. 550-561; XP055261094.
E. Rolls; Olfactory sensory-specific satiety in humans; Physiology and Behavior; vol. 61; No. 3; 1997; pp. 461-4 73; XP055261095.
Supplemental European Search Report dated Apr. 15, 2016 for related Appl. No. 14768448.4.
International Preliminary Report on Patentability and Written Opinion dated Sep. 24, 2015 for PCT/US2014/027510.

* cited by examiner

TASTE INHIBITION THROUGH THE USE OF AN AIR FLOW

CROSS REFERENCE TO RELATED APPLICATION

This application is a continuation of U.S. patent application Ser. No. 14/777,192 filed Sep. 15, 2015, which was a 371 of PCT/US2014/027510 filed Mar. 14, 2014, which claimed the benefit of U.S. Provisional Patent Application No. 61/789,310 filed Mar. 15, 2013 and U.S. Provisional Patent Application No. 61/789,041 filed Mar. 15, 2013, the priority of all applications is claimed and all applications are incorporated herein by reference.

BACKGROUND OF THE INVENTION

1. Field of the Invention

This invention relates to a method to suppress the appetite of a human by using a flow of air.

2. Related Art

It is know that flavor is conferred by two different sensory organs: the tongue and the nose. In order to experience the flavor of a food or beverage two processes must occur: olfaction and gustation. Gustation provides for a limited amount of information: sweet, sour, salty, bitter and umami. The rest of flavor is actually conferred by olfaction. Therefore olfaction plays an enormous role in one's ability to taste. Of course this is well known to anyone who has experienced nasal congestion from a cold. It becomes extremely difficult to taste one's food. The process of olfaction of food requires processes taking place on the back of the tongue, the nasopharynx and the olfactory bulb. As food or a beverage is chewed and heated inside the mouth, various aromatic compounds enter the vapor phase and these rise up through the nasopharynx and stimulate receptors of the olfactory nerve. This provides an important component of flavor. It is well established that diminished olfaction can lead to decreased appetite and food intake.

Methods to suppress appetite through inhalants are known, see for example, U.S. Patent Publications Nos. 2010/0239687; 2009/0197963; 2006/0222720; 2003/0012811; and U.S. Pat. Nos. 7,879,584; 4,521,427.

Method for directing a flow of air across or towards a human's face are known, see for example, U.S. Patent Publication No. 2004/0055601 and U.S. Pat. Nos. 7,036,502; 6,065,473; 5,561,862; 5,353,605; 2,560,215; 2,032,101.

SUMMARY OF THE INVENTION

Applicant has determined that a process which interferes with the passage of odorants from the back of the tongue to the olfactory bulb will diminish the flavor and taste of a food or beverage and diminish appetite. It is well established that diminished olfaction can lead to decreased appetite and food intake.

Obesity and its secondary medical complications is a significant health problem in many societies throughout the world. Therefore it is of interest to devise a process which can decrease the olfaction of food and beverages and consequently lead to a possible decrease in food and beverage intake for individuals with obesity. It is the object of this invention to decrease the olfaction of ingested foods and beverages by interfering with the transit of food and beverage odorants from the oral cavity up the nasopharynx to the olfactory bulb of the nasal cavity. The invention accomplishes this process by creating a continuous flow of air traveling into the nares and back towards the nasopharynx. This continuous air flow will be sufficient to cause convection of all the food and beverage odorants away from the olfactory bulb and towards the oropharynx. In other words the convection is sufficient to reverse the normal flow of food and beverage odorants from the back of the tongue into the nasopharynx and towards the olfactory bulb. This significantly limits the ability to appreciate the odors associated with a food or beverage being consumed. This in turn will significantly diminish the flavor of the food which will help in decreasing appetite for that food or beverage.

In addition to directing air into the nasal cavity air can be directed into the mouth. Of course there is a regular cycle of opening and closing the mouth during the ingestion of food or a beverage. This cannot be predicted and it may vary with the type of food or beverage being consumed as well as well as with the individual. However during the periods where the mouth is open air flow directed toward the mouth will enter and will travel from the opening of the mouth posteriorly toward the oropharynx and then directed towards the trachea and esophagus. The airflow velocity will be sufficient to convect the food and beverage odorants toward the trachea and esophagus and away from the nasopharynx. The majority of air directed towards the oropharynx will not travel towards the nasopharynx as that would necessitate a change in direction of over 90 degrees and also because the nasopharyngeal opening is smaller than the oropharyngeal opening and therefore poses much more resistance to air inflow. Thus air directed into the mouth will diminish the flow of food and beverage odorants into the nasopharynx and thus diminish their flavor and help to reduce the appetite for those foods and beverages.

It will be understood that the invention is not limited to a specific source of external air flow. Any means of moving air or creating a flow of air can be used including fans, compressors and sources of compressed air.

Specifically, the Invention can be defined as follows:
1. A method to suppress appetite of a human comprising: directing a flow of air at a face of the human and into a nose and/or a mouth of the human.
2. The method of item 1 wherein the flow of air at the face is about 10 to about 30 cubic feet per minute.
3. The method of item 2, wherein the flow of air is about 15 to 20 cubic feel per minute.
4. The method of item 1, wherein the air further comprises a fragrance.
5. The method of item 1, wherein the flow of air extends vertically upward from forehead to chin of the face.
6. The method of item 1, wherein the flow of air extends horizontally across the face from one side to the other side.
7. The method of item 5, wherein the flow of air has a direction which forms an angle of about 0° to 90° with 0° representing an angle directly vertical from the chin and °90 represents an angle pointed directly at the face.
8. The method of item 7, wherein the angle is about 0 to about 45°.
9. The method of item 1, wherein the flow of air has a direction which forms an angle of greater than about 0° to 90° with 0° representing an angle across the face of a person and 90° representing an angle that points directly at the face.

10. The method of item 5, wherein the angle is about 45° to 90°.

11. The method of item 1, wherein the flow extends about 3 to 12 inches.

12. The method of item 1, wherein the flow starts about 1 to about 6 inches from a plane of the face.

13. The method of item 1, wherein the flow of air is conical in shape.

14. A method whereby an air flow is directed from outside a body into the nose and/or the mouth to diminish the flow of food and beverage odorants form the oropharynx towards the olfactory bulb thereby decreasing the flavor of the food.

15. The method of item 14 whereby decreasing the flavor of a food or beverage also decreases the appetite for that food or beverage.

16. The method of item 14, wherein air flow is parallel to the plane of the face and directed at an angle from 0 (horizontal) to 90 degrees (directed towards the face) so that the air flow enter into the nares.

17. The method of item 14, wherein the air flow is directly towards the face and at an angle of 90° degrees (pointing straight up from the chin) to 90° (horizontal directly at the face) so that the air flows from outside the body upwards into the nares and then directed backwards towards the nasopharynx.

18. The method of item 14, wherein a nasal cannula is used to direct air flow directly into the nares so that it can travel towards the nasopharynx.

19. The method of item 14 where the airflow is vertical and directed towards the mouth so that the air flow travels to the posterior oropharynx and convect the food and beverage odorants away from the nasopharynx.

20. The method of item 10, wherein the air flow is about 6 cubic feet per minute or more.

An apparatus suitable for accomplishing this method is taught in U.S. Pat. No. 7,036,502, the contents of which are incorporated herein by reference, except for the fact that the direction of the airflow in the '502 patent is across the face while in the present Invention, the direction of the air flow is at the face and into the nose and/or mouth.

DETAILED DESCRIPTION OF THE INVENTION

Figure 1:
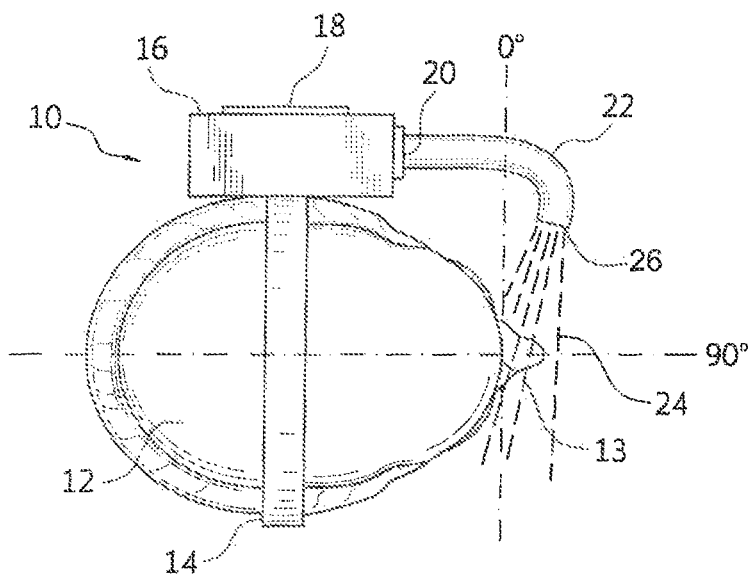
FIG. 1 is a top view of a human face wearing a device which directs a flow of air at the face.

Turning to FIG. 1, device 10 of the present invention is worn on head 12 of a human being. Device 10 comprises headset 14 to which is mounted fan 16. Fan 16 has inlet 18 and outlet 20. Fixed to outlet 20 is flexible tubing 22. Outlet 20 has a manifold to mate square outlet 20 to circular tubing 22. Fan 16 with tubing 22 generates a flow of air 24 at face 13 of the human head 12. Outlet 26 of flexible tubing 22 is spaced 1 to 6 inches from the plane of the face.

Figure 2:
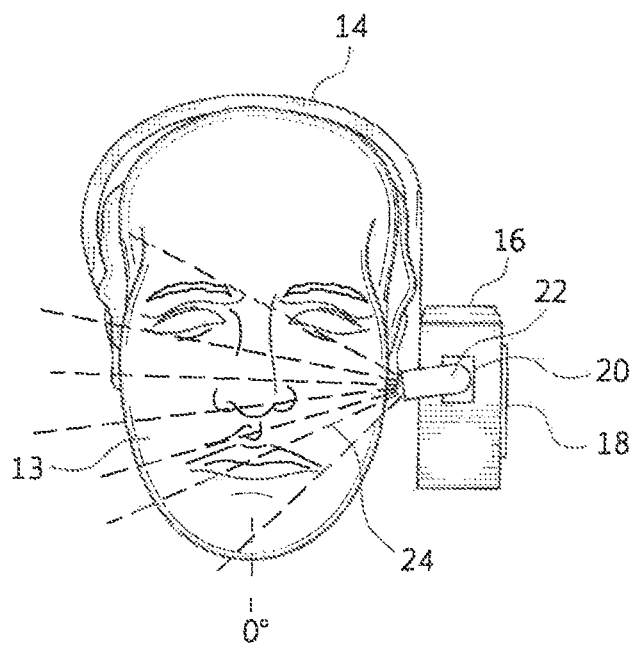
FIG. 2 is a front view of FIG. 1 where the flow of air is directed horizontally across the face.

The horizontal orientation of the head with respect to the device is shown by the coordinate 0° and 90° in FIG. 1 while the vertical orientation to the head is shown in FIG. 2 by the coordinate 0°. For the vertical orientation, 90° is the same as shown in FIG. 2.

In FIG. 2, a front view of face 13 is shown. As will be appreciated, air flow 24 has a generally conical cross section.

Figure 3:
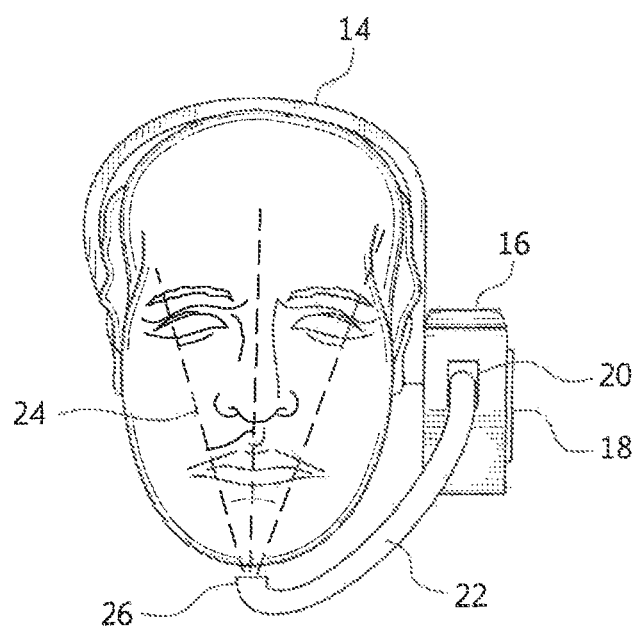
FIG. 3 is a front view of FIG. 1 wherein the flow of air is directed vertically up the face from the chin.

FIG. 3 illustrates the preferred embodiment where air flow 24 starts below or at the chin and flows vertically upward towards the forehead. In FIG. 3, flexible tubing 22 has been bent to position outlet 26 at or below the chin.

Flexible tubing 22 allows for the positioning of outlet 26 at different positions. Suitably, the length of the air flow from outlet 26 to where it dissipates is 3 to 12 inches.

Scent can be introduced into the air flow.

It has been found that the air flow reduces the amount of air exhaled through the nose. Olfaction occurs when there is exhalation of scent from food on the tongue through the nose. Thus, the flow of air diminishes olfaction.

The addition of scent to the air flow helps to further reduce olfaction, thereby further suppressing appetite.

The flow of air is used to diminish the transport of comestible odorants from the back of the tongue to the olfactory receptors in the nose. If one consumes some food or beverage while air is blown at the face one will immediately notice a substantial diminution of the flavor of that comestible.

In order to accomplish this air has to be blown into the nares (opening of the nose) and into the mouth. In order to accomplish this the air flow is directed so it enters the nose and the mouth. For the mouth any air flow that has some velocity component that is directed into the mouth will work. In the horizontal orientation, 0° represents the direction parallel to the face and 90 degrees represent the angle that points directly at the face. Airflow that has a direction greater than 0 degrees to the face will work. However the closer the angle approaches 90 degrees the more effective it will be. The other angular coordinate is the angle with respect to the horizon. The most effective will be a source that is vertical from the chin upward but any air source which lies between straight up and straight down can work.

The airflow that goes into the nose must have a direction such that it has a velocity component that points directly upwards. As in the case of the airflow into the mouth any air flow direction that has some velocity component that is directed towards the nose will work.

It will be understood that the claims are intended to cover all changes and modifications of the preferred embodiments of the invention herein chosen for the purpose of illustration which do not constitute a departure from the spirit and scope of the invention.

I claim:

1. A method to suppress appetite of a human comprising:
   causing a convective flow of air into a nose toward an oropharynx of the human during consumption of food or beverage by the human, thereby causing a reduction in a flow of food and beverage odorants from an oral cavity up a nasopharynx to an olfactory bulb of the human, wherein causing the convective flow of air into a nose toward an oropharynx of the human comprises:
   directing, by a device worn on a head of the human, a flow of air at a face of the human and into the nose of the human during the consumption of food or beverage, wherein the flow of air has a direction which forms an angle between greater than 0° and 90°, with 0° representing an angle pointed horizontally from one ear to another ear across the face and 90° representing an angle pointed directly at the face, wherein the device comprises a headset, a fan, and a tube, and is adapted to direct air at the face of the human and into the nose of the human during the consumption of food or beverage.

2. The method of claim 1 wherein the flow of air is between 6 and 30 cubic feet per minute.

3. The method of claim 2, wherein the flow of air is between 15 and 20 cubic feet per minute.

4. The method of claim 1, wherein the air further comprises a fragrance.

5. The method of claim 1, wherein the angle is between greater than 0 and 45°.

6. The method of claim 1, wherein the angle is between 45° and 90°.

7. The method of claim 1, wherein the flow extends between 3 and 12 inches.

8. The method of claim 1, wherein the flow starts between 1 and 6 inches from a plane of the face.

9. The method of claim 1, wherein the flow of air is conical in shape.

10. A method to suppress appetite of a human comprising:
causing a convective flow of air into a nose toward an oropharynx of the human during consumption of food or beverage by the human, thereby causing a reduction in a flow of food and beverage odorants from an oral cavity up a nasopharynx to an olfactory bulb of the human, wherein causing the convective flow of air into a nose toward an oropharynx of the human comprises: directing, by a device worn on a head of the human, a flow of air at a face of the human and into the nose of the human during the consumption of food or beverage, wherein the device comprises a headset, a fan, and a tube, and is adapted to direct air at the face of the human and into the nose of the human during the consumption of food or beverage.

11. The method of claim 10 wherein the flow of air is between 6 and 30 cubic feet per minute.

12. The method of claim 11, wherein the flow of air is between 15 and 20 cubic feet per minute.

13. The method of claim 10, wherein the air further comprises a fragrance.

14. The method of claim 10, wherein the flow extends between 3 and 12 inches.

15. The method of claim 10, wherein the flow starts between 1 and 6 inches from a plane of the face.

16. The method of claim 10, wherein the flow of air is conical in shape.

17. A method to suppress appetite of a human comprising directing a flow of air, by a device worn on a head of the human, during consumption of food or beverage, from outside a body of the human into a nose of the human to cause a convective flow of air into the nose toward the oropharynx and thereby diminish the flow of food and beverage odorants from an oral cavity up a nasopharynx to the olfactory bulb thereby decreasing flavor of the food or beverage and decreasing appetite of the human for the food or beverage during consumption of food or beverage by the human, wherein the device comprises a headset, a fan, and a tube, and is adapted to direct air at the face of the human and into the nose of the human during the consumption of food or beverage.

* * * * *